United States Patent [19]

Wilson

[11] Patent Number: 4,964,418

[45] Date of Patent: Oct. 23, 1990

[54] COLLAPSIBLE CERVICAL IMMOBILIZATION DEVICE

[76] Inventor: Maximilian J. Wilson, 5834 E. 62 Pl., Tulsa, Okla. 74136

[21] Appl. No.: 157,035

[22] Filed: Feb. 16, 1988

[51] Int. Cl.⁵ ............................................. A61F 13/00
[52] U.S. Cl. ............................ 128/857; 128/DIG. 23
[58] Field of Search ............... 128/133, 134, 78, 87 R, 128/87 B, 88, 133, 134, 857, DIG. 23; 5/81 R, 82 R, 82 B, 89, 434, 435, 436, 437; 269/328

[56] References Cited

U.S. PATENT DOCUMENTS

| | | | |
|---|---|---|---|
| 3,017,221 | 1/1962 | Emery | 5/437 |
| 3,897,777 | 8/1975 | Morrison | 128/133 |
| 4,034,748 | 7/1977 | Winner | 5/82 R |
| 4,182,322 | 1/1980 | Miller | 5/82 R |
| 4,297,994 | 11/1981 | Bashaw | 128/133 |
| 4,528,981 | 7/1985 | Behar | 128/133 |
| 4,571,757 | 2/1986 | Zolecki | 128/133 |
| 4,589,407 | 5/1986 | Koledin et al. | 128/134 |
| 4,612,678 | 9/1986 | Fitsch | 5/82 R |
| 4,640,275 | 2/1987 | Buzzese et al. | 5/437 |
| 4,655,206 | 4/1987 | Moody | 128/134 |
| 4,665,908 | 5/1987 | Calkin | 128/134 |

Primary Examiner—Mickey Yu
Assistant Examiner—Charles H. Sam

[57] ABSTRACT

A collapsible cervical cervical immobilization device comprising two pieces of treated fiberboard. The pieces are placed one on top of the other and joined together at the center of each. The upper member consisting of different sections formed by and attached to each often by fold lines. The fold lines allow these sections to be rotated independent of each other with the fold lines acting as a hinge. When certain sections are folded against a patient's head they form a cradling area. When the rigid shoulder sections are mated to the base member by means of Velcro-type hook-loop fasteners the device becomes rigid thus restraining the patients head and neck area. Adhesive tape on the bottom of the base member allows for the device to be secured to a surface that further supports the patients cervical area.

2 Claims, 3 Drawing Sheets

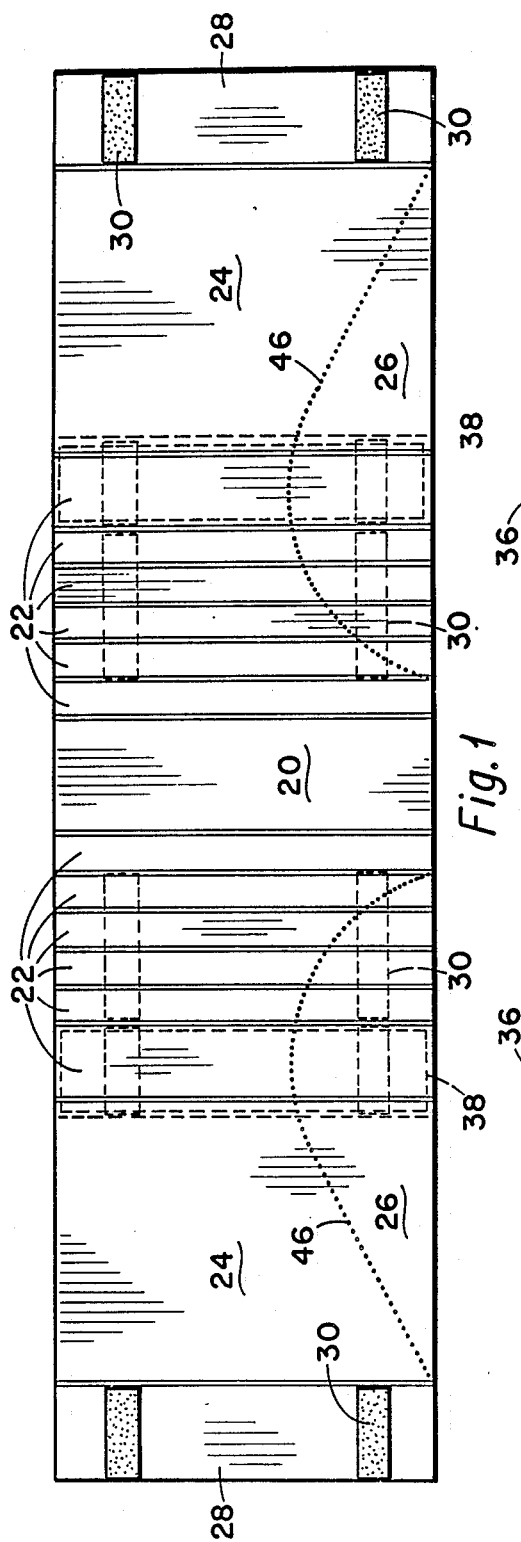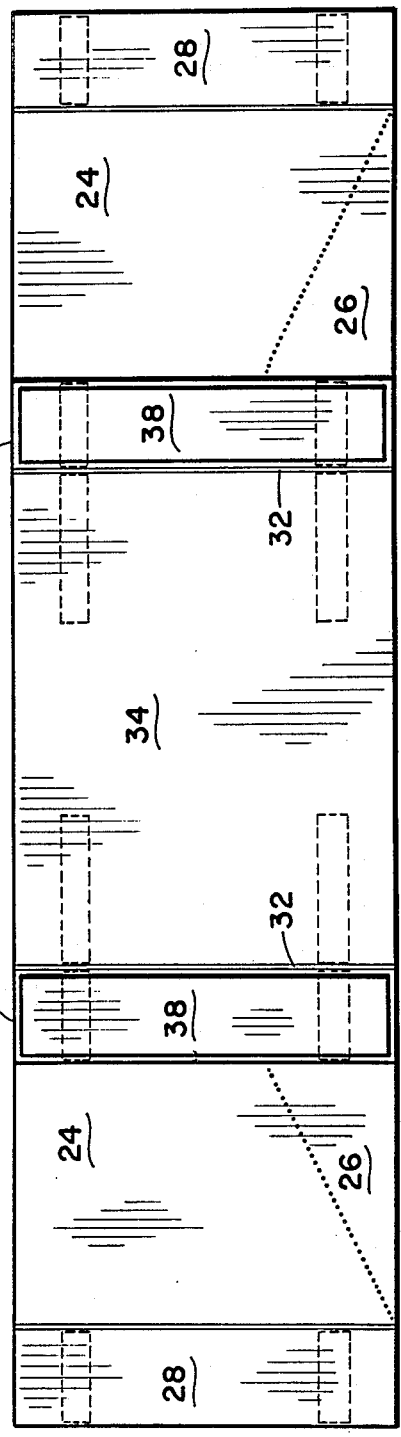

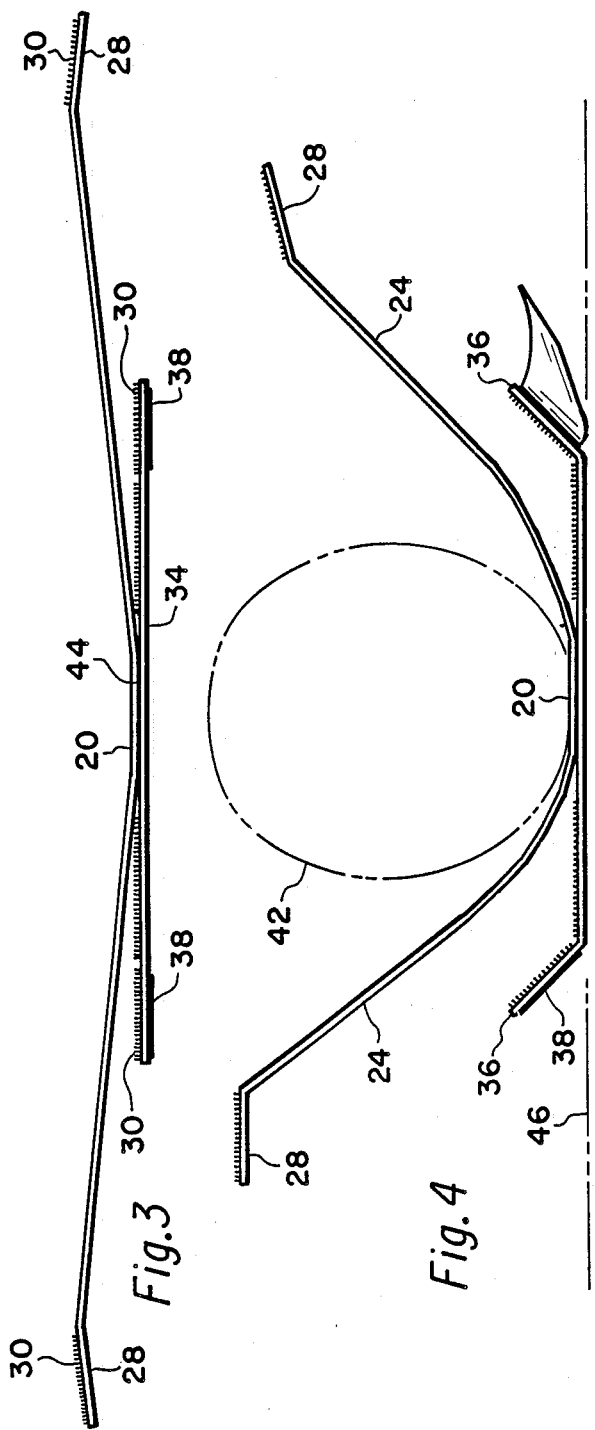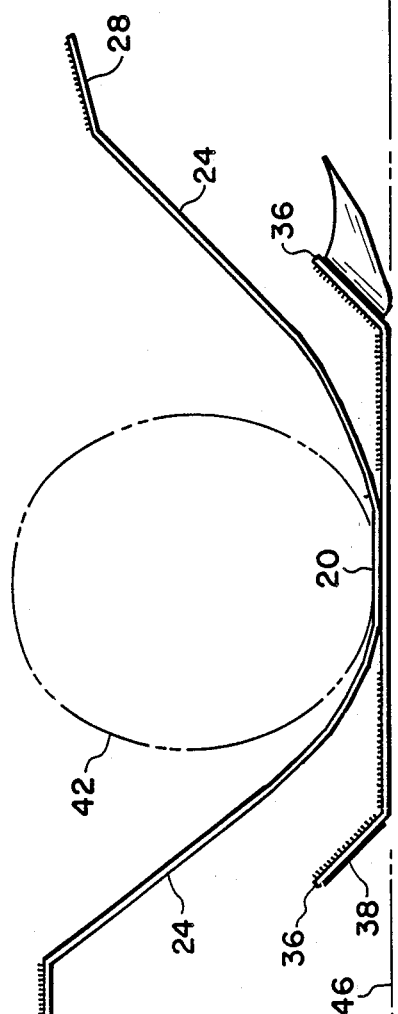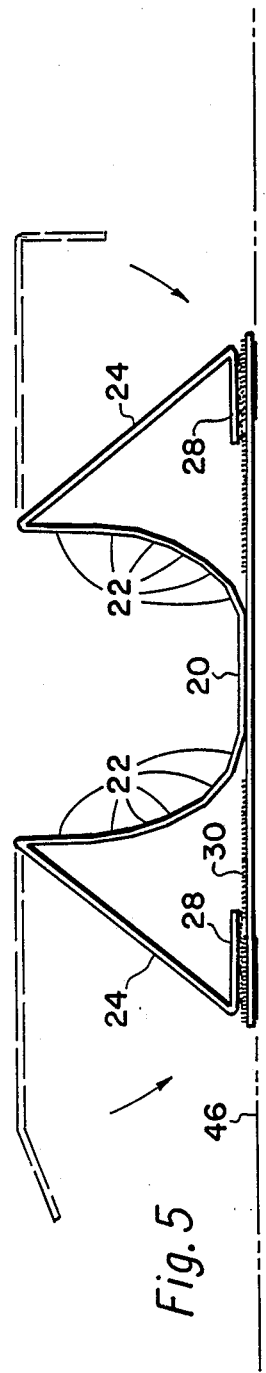

COLLAPSIBLE CERVICAL IMMOBILIZATION DEVICE

BACKGROUND—FIELD OF INVENTION

This invention relates to medical devices, especially restraints for use in immobilizing a patient's head and neck to prevent injurious motion which would aggravate existing injuries and/or prevent new injuries caused by head and neck motion.

BACKGROUND—DESCRIPTION OF PRIOR ART

Heretofore a wide variety of restraining and immobilizing devices have been proposed and implemented for immobilizing the head and neck of an injured person.

U.S. Pat. No. 4,640,275 shows a device consisting of vertical side plates which do not contour to the patients head thus allowing some degree of rotation of the head. Only one side is adjustable requiring movement of the patient's head to allow for the device to be secured. This device also requires a backboard of certain dimensions to allow for the receiving channel on the device to attach the device to the backboard.

U.S. Pat. No. 4,182,322 shows a head-restraining and safety support device that requires a special splint/letter apparatus by means of Velcro surfaces, snap fasteners, or buckle fasteners. U.S. Pat. No. 4,297,994 shows a device that utilizes cushions made of foam rubber type materials that can not be compressed thus requiring a relatively large area for storage.

All of the cited patents are intended for re-use thus allowing for the possibility of cross infection. Their design and construction make them difficult if not impossible to clean especially after contact with body fluids.

OBJECTS AND ADVANTAGES

Accordingly, several objects and advantages of my invention are: (1) to provide a device that can be easily applied to a patient with minimal movement of that patient, (2) to provide a device that can be used to secure a patient's head and neck area after that patient has been placed upon an apparatus that will be used to support his cervical area, (3) to provide a device that is adjustable allowing for differing head sizes and one that can be utilized on patients that are wearing protective helmets, (4) to provide a device that can be secured to a litter, stretcher, table or any relatively flat surface that will support the patient's cervical area without that surface or apparatus being specially prepared to accept the device, (5) to provide a device that is collapsible thus requiring a relatively small storage space, (6) to provide a device that contours to the patient's head thus providing greater immobilizing characteristics, (7) to provide a device that is relatively inexpensive thus disposable after use, lessening the chance of cross infection, (8) to provide a device that can be made of light weight materials which would be advantageous in situations where weight is a concern such as use in aircraft, (9) to provide a device that can be used in conjunction with and will not interfere with a cervical neck brace.

Readers will find further objects and advantages of the invention from a consideration of the ensuing description and accompanying drawings.

DRAWING FIGURES

FIG. 1 shows a top plan view of the invention.
FIG. 2 shows a bottom plan view of the invention.
FIG. 3 shows a front elevational view of the invention with the upper member elevated for clarity of disclosure.
FIG. 4 shows a front elevational View of the invention, with a phantom head in position, illustrating a step in the method of applying the invention.
FIG. 5 shows a front elevational view of the invention in the immobilizing position, except with no head restrained there by for clarify of disclosure. Phantom lines also depict the shoulder and end flaps of the upper member and their direction of rotation in the method of applying the invention.
FIG. 6 shows a perspective view of one embodiment of the invention in the immobilizing position with no head restrained there by for clarity of disclosure.
FIG. 7 shows a perspective view of the invention with the removable sections removed and with no head restrained there by for clarity of disclosure.

DRAWING REFERENCE NUMERALS 20 center section of upper member
22 contouring sections
24 shoulder sections
26 removable sections
28 end flaps of upper member
30 strips of Velcro type Hook-Loop fasteners
32 fold lines
34 center section of base member
36 end flaps of base member
38 double sided adhesive tape
40 protective backing
42 head
44 joined section
46 perforation line
48 cervical support surface

DETAILED DESCRIPTION OF THE INVENTION

Figure 6:
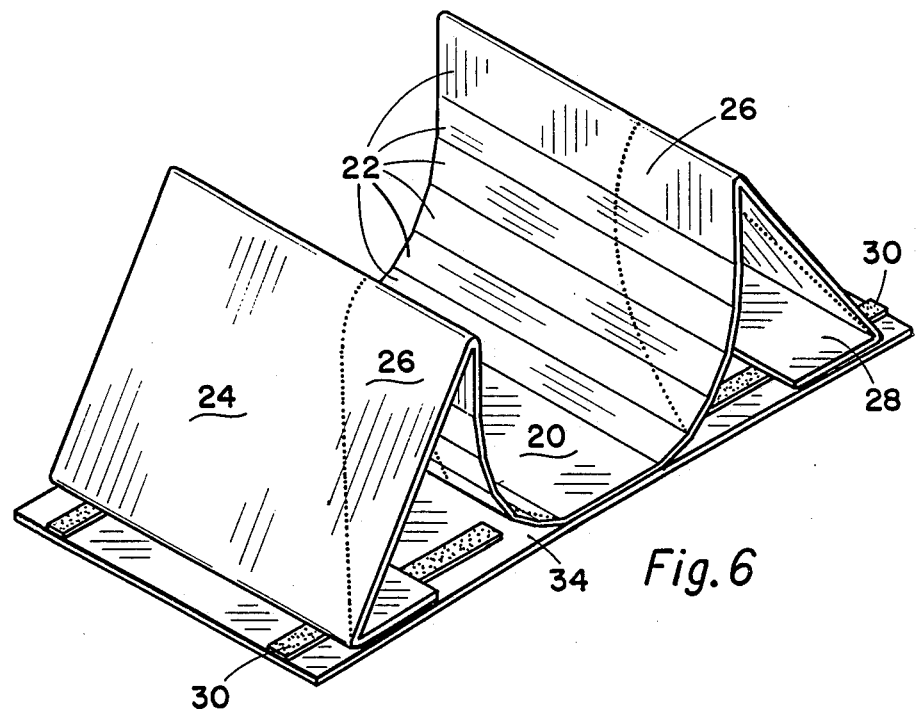
Figure 7:
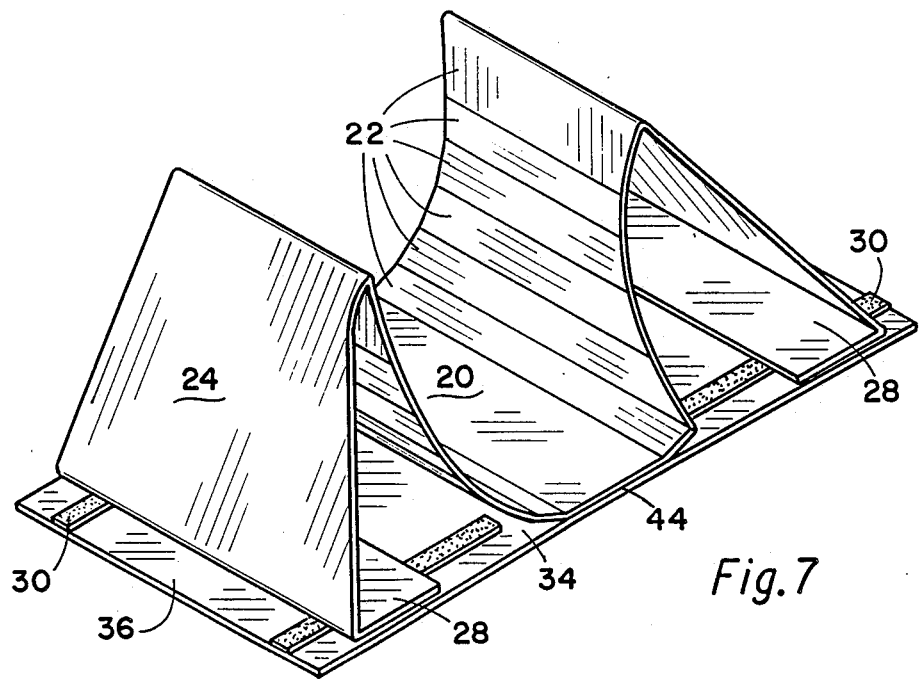

The device consists of two pieces of paraffin coated fiberboard. These members, the upper and base members, are joined together at the center of each 44. They are joined by a piece of double sided adhesive tape that is placed along a line parallel to the center width of each. The upper member is positioned so that it is in position above the base member.

The upper member consists of a rectangular piece of fiberboard separated into different sections by fold lines 32. The fold lines are made by scoring or compressing the fiberboard along lines that are perpendicular to the length of the upper member. The sections formed by these fold lines are the two end flaps 28, the contouring sections 22, the two shoulder sections 24, and the center section 20. Two removable sections 26 are outlined by perforation lines 46 in the fiberboard. The removable sections extend into the shoulder and contouring sections of the upper member. Strips of Velcro type hookloop fasteners 30 are attached by adhesive to the top of the upper member end flaps 28 in positions so that they mate with strips of Velcro type hook-loop fasteners that are attached to the base member.

The base member is a rectangular piece of fiberboard separated into three sections by fold lines 32. The three sections are the center section 34 and the two end flaps 36. Double sided adhesive tape 38 is attached parallel to the fold line and on the bottom of the end flaps. Removable protective backing 40 is left in position on the exposed or bottom side of the adhesive tape. Sections of Velcro type hook-loop fasteners 30 are attached lengthwise to and on the top of the base member. Their position corresponds to the position of the mating Velcro type hook-loop fasteners on the end flaps of the upper member.

While the above description contains many specificities. the reader should not construe these as limitations on the scope of the invention, but merely as exemplifications of preferred embodiments thereof. Those skilled in the art will envision many other possible variations are with its scope. For example skilled artisans will readily be able to change the dimensions and shapes of the various embodiments. They will also be able to make the device of alternative materials such as plastics, wood, metal, cloth or composite materials or a combination of any or all. They can use a different type of adhesive or process to join the upper and base members. They can change the size or shape of the removable sections or construct the device with these omitted. The number of and dimensions of the contouring sections can also be changed. The device can also be made with tape stris or Velcro type hook-loop fasteners that connect the two shoulder sections after the device has been applied. Foam or some other type of material used for padding can be secured to the contouring sections and upper member center section to cushion the patient's head. Alternative means of attaching the device to a cervical support base such as Velcro type hook-loop fasteners could also be utilized. Accordingly the reader is requested to determine the scope of the invention by the appended claims and their legal equivalents, and not by the examples which have been given.

OPERATION OF THE INVENTION

If the device is to be applied to a patient that is wearing a cervical collar, the two removable sections 26 are removed by separating them from the upper member at the perforated lines 46. The device is then placed in a flattened position and slid under the patient's head 42. After the device is in position under the patient's head both sides of the upper member are rotated towards the vertical position. This is performed to ensure that the device is not under the patient's shoulders. After ensuring that the device is the desired position relative to the patient and cervical supporting surface, the end flaps of the base member 36 are rotated from the horizontal to the vertical position to expose the tape 38 on the base. Then the protective backing 40 on the tape is removed to expose the adhesive on the tape. Then the base flaps are rotated back to the horizontal position are pressed down to secure the device to the supporting surface, 48, by means of the adhesive on the tape.

The contouring sections 22 of the upper member are then folded to contact the sides of the patient's head. With the contouring sections in place the shoulder sections and end flaps are rotated downward toward the base. After achieving the desired rigidity of the device, the Velcro type hook-loop fasteners on the upper member end flaps and base member are pressed together to secure the device in the immobilizing position.

The combination of the contouring sections 22 against the patients head, 42 the device being secured to a cervical support surface 48, and the rigidity of shoulder sections 24 do not allow the patient to move his head thus immobilizing the patients head and neck area.

Having thus described my invention, I now claim:

1. A collapsible cervical immobilization device for restraining the head and neck of an injured person, said device comprising:
   An upper member and base member, each separated into multiple interconnected sections by hinges and wherein said upper member and base member are connected to each other, at their center sections; wherein the head and neck are supported and restrained by opposing sections of the device's upper member when folded into the desired position and secured to the base member by means of Velcro-type hook-loop fasteners attached to said upper member and base member.

2. A device of claim 1 wherein said hinges are folds in said upper member and said base member.

* * * * *